United States Patent [19]

Evans et al.

[11] Patent Number: 5,840,932
[45] Date of Patent: Nov. 24, 1998

[54] PROCESS FOR ETHYLENE OXIDE PRODUCTION

[75] Inventors: Wayne Errol Evans, Richmond; Thomas Records Keller, III, Houston, both of Tex.

[73] Assignee: Shell Oil Company, Houston, Tex.

[21] Appl. No.: 859,875

[22] Filed: May 21, 1997

Related U.S. Application Data

[60] Provisional application No. 60/018,049, May 21, 1996.
[51] Int. Cl.$^6$ .................................................. C07D 303/00
[52] U.S. Cl. ............................................................ 549/512
[58] Field of Search ................................................ 549/512

[56] References Cited

U.S. PATENT DOCUMENTS 4,921,681   5/1990   Ozero et al. ............................ 422/197

*Primary Examiner*—Amelia Owens
*Attorney, Agent, or Firm*—Fredrik Marlowe

[57] ABSTRACT

This invention relates to the novel recycle of a slipstream of product gas from the reactor outlet train, the slipstream having been cooled to a lower temperature, back into the outlet head. The recycled cooled gas immediately reduces the temperature of the product gas as the product gas exits the reactor tubes.

10 Claims, 4 Drawing Sheets

RECYCLE SLIPSTREAM FROM ANY CONFIGURATION IN FIG. 1, 2, OR 3

PROCESS FOR ETHYLENE OXIDE PRODUCTION

This application claims the benefit of the filing of U.S. provisional patent application Ser. No. 60/018,049, filed May 21, 1996, relating to a process for ethylene oxide production.

FIELD OF THE INVENTION

The invention relates to a process for ethylene oxide production, in particular ethylene oxide catalyst.

BACKGROUND OF THE INVENTION

As ethylene oxide catalysts age, the reactor temperature required to maintain production increases. Two problems frequently result from elevated temperatures, particularly for the inherently higher operating temperatures of high selectivity catalysts: (1) temperature-related formaldehyde and acetaldehyde formation are initiated, typically at exit gas temperatures of 250°–260° C.; and (2) the explosive nature of the exit gas imposes limitations on the allowable levels of oxygen and ethylene in the feed gas. These "flammable limits" are dependent upon a number of parameters, most notably the exit gas temperature. Each of the cited problems can have a profound impact on plant operation and profitability.

High purity ethylene oxide and the ethylene oxide used to make fiber grade ethylene glycol are subject to severe aldehyde restrictions. Levels of 10 ppm for total aldehydes in the ethylene oxide final product are typical. The inherent susceptibility of any particular ethylene oxide plant to aldehyde generation depends on the metallurgy and design of the ethylene oxide (EO) reactor outlet train. A large fraction of plants can suffer excessive aldehyde generation at high operating temperatures. Following the onset of aldehyde generation, aldehyde levels climb rapidly as operating temperature continues to increase. The limited options for combating aldehyde contamination are costly. One option is that the catalyst temperature may be suppressed, with a concomitant loss of daily production. A second option is to prematurely recatalyze the unit. A third option is to retrofit the outlet section of the reactor coolant chamber with a "post-cooler." This method has proven to be effective at reducing outlet gas temperatures at an EO plant of assignee, but such retrofits are prohibitively expensive. Another option proven to be effective is to retrofit the outlet piping with cooling jackets or cooling coil insertions. Also, catalyst choice may be restricted to only catalysts of very high activity.

The concentrations of oxygen and ethylene in the reactor feed gas for an ethylene oxide plant are dictated by the oxygen and ethylene flammable limit concentrations in the inlet and outlet gas, which are a function of the outlet gas temperature. For higher outlet gas temperatures, the permissible levels of feedstock oxygen and ethylene are lower. As feed oxygen and ethylene concentrations are reduced, the process selectivity declines and the apparent catalyst activity declines (i.e., temperature required to maintain production rises). Thus, suppressed oxygen and ethylene feed levels reduce profitability.

PRIOR ART

Nippon Shokubai's JP 07-188-199-A, "Preparation of Ethylene Oxide with Reduction of Undesired Reactions" discloses vapor phase catalytic oxidation of ethylene with oxygen and dilution of reaction product with inert gas. The Nippon abstract describes a system in which the outlet stream after exiting the outlet head is mixed with "inert gas, especially N2", to dilute the gas stream. A claimed advantage is that undesired reactions such as isomerization to acetaldehyde, etc., is reduced by dilution with inert gas. The inert gas may be nitrogen, carbon dioxide, methane, argon, etc., preferably nitrogen. Injection of inert gas requires removal of the gas prior to recycle, as well as the upsizing of downstream hardware. These requirements become prohibitively expensive if the outlet stream is diluted to any meaningful degree. In the instant invention, the product stream composition is not altered, except that the formation of contaminating aldehydes is suppressed. The instant invention utilizes cooling of the outlet gas stream to suppress aldehyde formation, a different mechanisms of changing gas phase chemistry than dilution. The cooling method of the disclosed invention is more effective for suppressing undesirable aldehyde formation. The preferred configurations for the instant invention involve injection of the recycled gas directly into the outlet head.

U.S. Pat. No. 4,921,681 to Ozero et al., incorporated hereinto by reference, discloses an ethylene oxide reactor having a lower cooling zone and a distribution zone below that. Tubes within the cooling zone are packed with inert particles, and are empty within the distribution zone. The present invention does not inject recycle feed coolant around the tubes.

U.S. Pat. No. 4,874,879 to Lauritzen et al., incorporated hereinto by reference, relates to a process for starting up an ethylene oxide reactor.

SUMMARY OF THE INVENTION

This invention relates to the novel recycle of a slipstream of product gas from the reactor outlet train, the slipstream having been cooled to a lower temperature, back into the outlet head. The recycled cooled gas immediately reduces the temperature of the product gas as the product gas exits the reactor tubes. Benefits of the process have economic and strategic implications.

The process essentially eliminates temperature-related aldehyde formation between the reactor tube exit and the product heat exchanger. Depending on the specific situation, plants benefit from one or more of the following: (1) improved product quality; (2) avoidance of reduced production levels related to product quality; and (3) extended catalyst life. Further, the use of high selectivity catalysts become an option that is currently unavailable to plants that are prone to temperature-related aldehyde problems.

The process also improves limitations placed on feed ethylene and oxygen concentrations which are imposed by the temperature-dependent "flammable limits" of the product gas in the outlet head. This limitation improvement allows operation at higher oxygen and/or ethylene levels, thereby improving catalyst activity, selectivity and stability.

The process is more effective and less expensive to deploy and operate, particularly as a retrofit, than other methods of reducing aldehyde generation such as forced kerosene post-cooling zone, placement of chilled heat exchange tubes within outlet head or outlet pipes, fitting of outlet pipes with cooling jackets, or injection of inert gas into outlet pipes.

DESCRIPTION OF THE INVENTION

According to the instant invention, a portion of the cooled product stream is directed back into the outlet head by, for example, nozzles that effect rapid mixing with the outlet gas as it emerges from the reactor tubes into the outlet head. In this manner, the temperature of the outlet head contents is substantially reduced.

Figure 1:
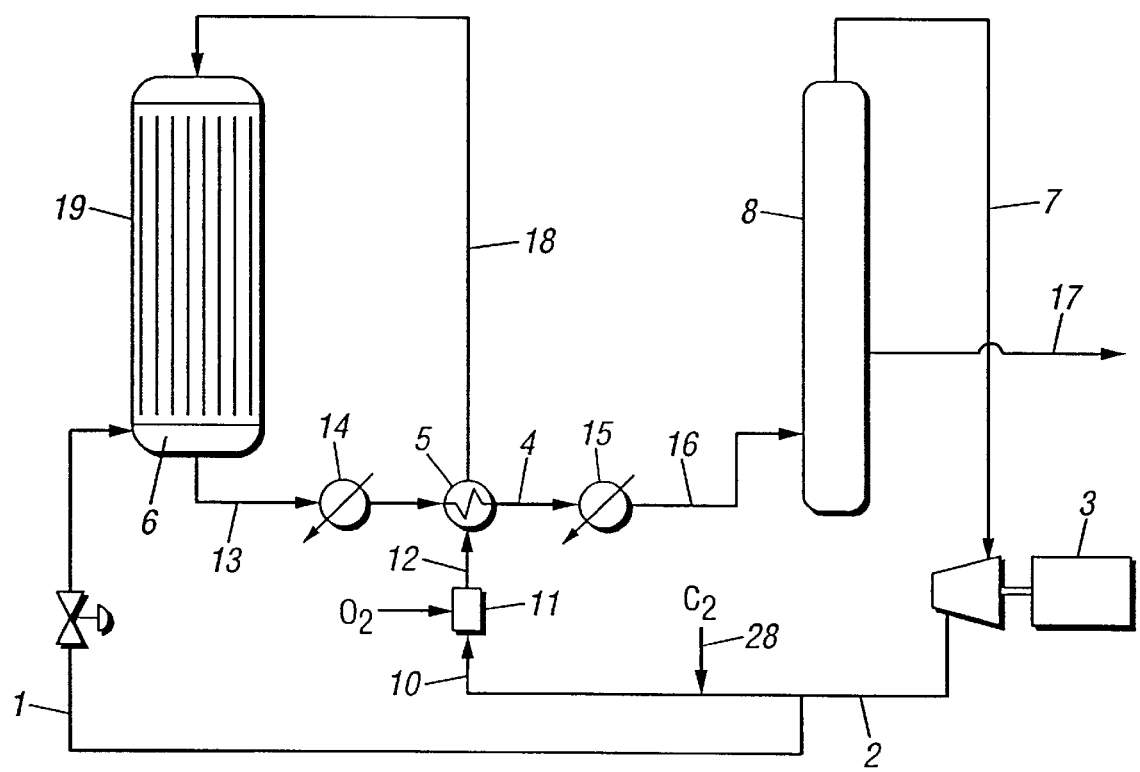
FIG. 1 is a preferred configuration of the process stream.

In the preferred configuration (FIG. 1), cooled recycle slipstream (temperature 27° to 54° C. (80° to 130° F.)) from the outlet 2 of the recycle gas compressor 3 or the cooled product gas 4 (temperature 107° to 190° C. (225° to 375° F.)) from the exit of reactor feed/product heat exchanger 5 is sent to the outlet head 6 of reactor 19. In this configuration, the slipstream is already cooled by existing hardware. The only additional hardware requirements are a blower (not required for the recycle gas option), a nozzle system (not shown) by which the slipstream 1 is injected into the outlet head 6, pipe, and associated process control and safety-related items. Recycle gas compressor 3 receives stream 7 (temperature 16° to 31° C. (60° to 88° F.)) which is split into recycle slip stream 1, as mentioned, and stream 10 is mixed with oxygen in vessel 11. Feed stream 12 is heat exchanged in reactor feed/product heat exchanger 5 with product stream 13 (temperature 232° to 302° C. (450° to 575° F.)) which is cooled to a temperature of 163° to 232° C. (325° to 450° F.) in primary product cooler 14. Secondary product cooler 15 cools stream 4 (temperature 107° to 190° C. (225° to 375° F.)) coming from feed/product heat exchanger 5. Stream 16 is admitted to EO absorber 8 and product stream 17 is removed. Feed stream 18 (temperature 93° to 177° C. (200° to 350° F.)) is admitted to EO reactor 19. It is important that stream 1 be admitted below the catalyst tubes in vessel 19. The ratio of slipstream 1 to product stream 13 is 1:20 to 1:1. Ethylene is introduced to the process via line 28 intermediate the compressor 3 and the chamber 11 for admitting oxygen. Some ethylene oxide plants incorporate more than one product cooling exchanger. In such cases, the slipstream could be taken from the outlet region of any of the exchangers.

Figure 2:
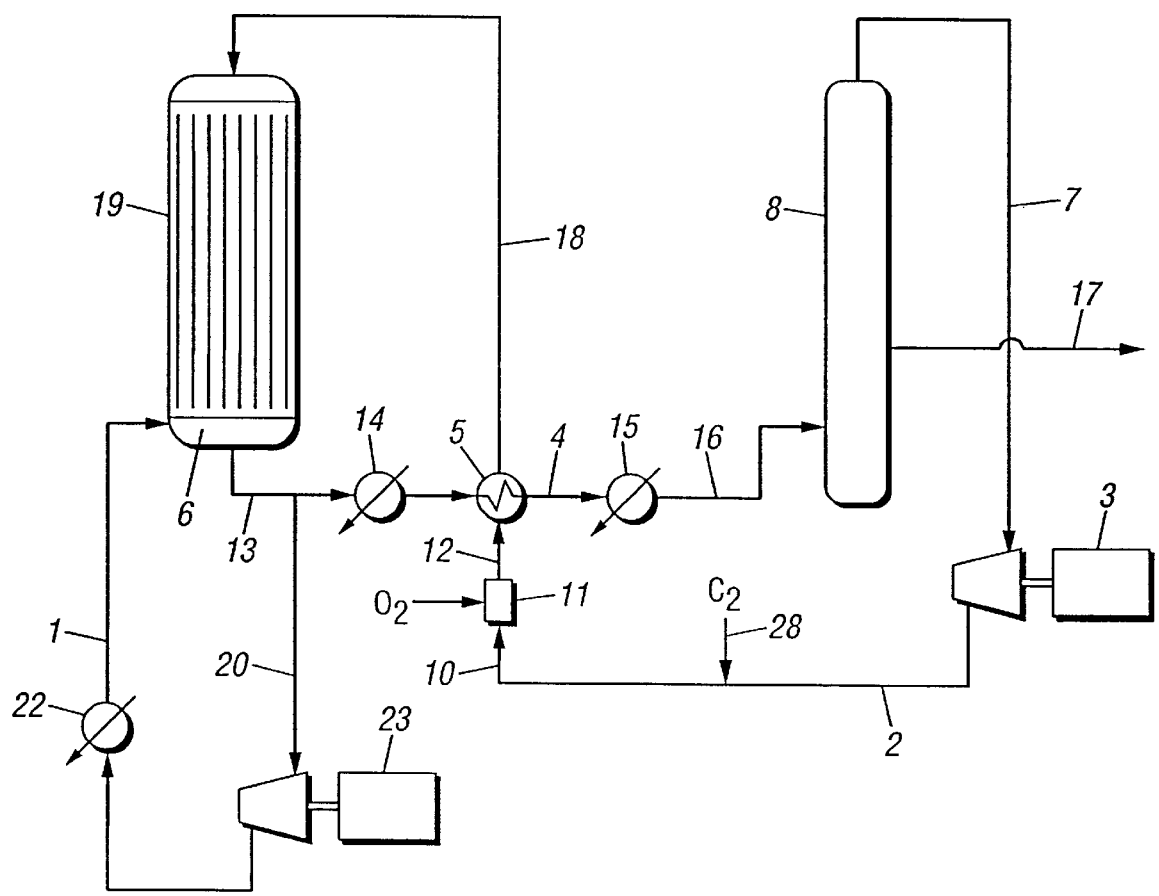
FIG. 2 shows an alternative configuration of FIG. 1.

In an alternative configuration (FIG. 2), the outlet slipstream 20 is collected ahead of the primary product cooler heat exchanger(s) 14. In this configuration, an additional cooling exchanger 22 would be required to reduce the temperature of recycled slipstream 20.

Figure 3:
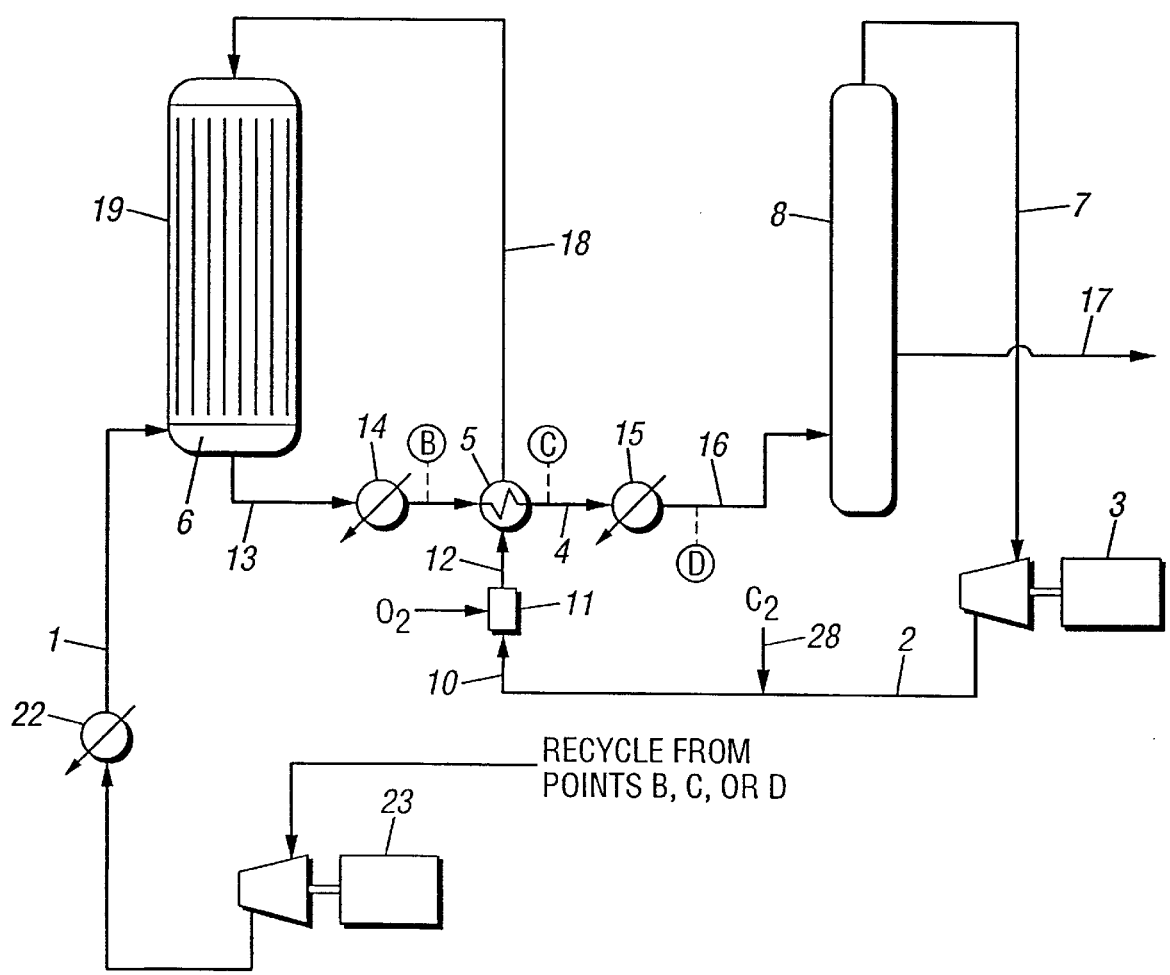
FIG. 3 shows a second alternative configuration of FIG. 1.

In another alternative configuration (FIG. 3), configurations 1 and 2 are combined by recycling cooled slipstream from the outlet of either the primary product cooler 14, the feed/product exchanger 5, or the secondary product cooler 15. In each of the above examples, it is tacitly assumed that the outlet slipstream recycle 21 is pressurized only enough to provide adequate mixing and an adequate recycle ratio to accomplish the desired cooling. Inclusion of an auxiliary recycle cooler 22 is an option for this configuration to reduce the slipstream flow that is required to achieve the desired temperature in stream 13. Alternatively, it would be possible to pressurize the outlet slipstream recycle to higher pressures and reduce the nozzle hole bore size(s). This would result in a rapid pressure drop as the recycle stream entered the outlet head. Adiabatic cooling, the degree of which is related to the amount of pressure drop, would further cool the outlet chamber. The advantage of this option would be that a smaller recycle ratio could accomplish the same degree of cooling as with the low pressure option.

Figure 4:
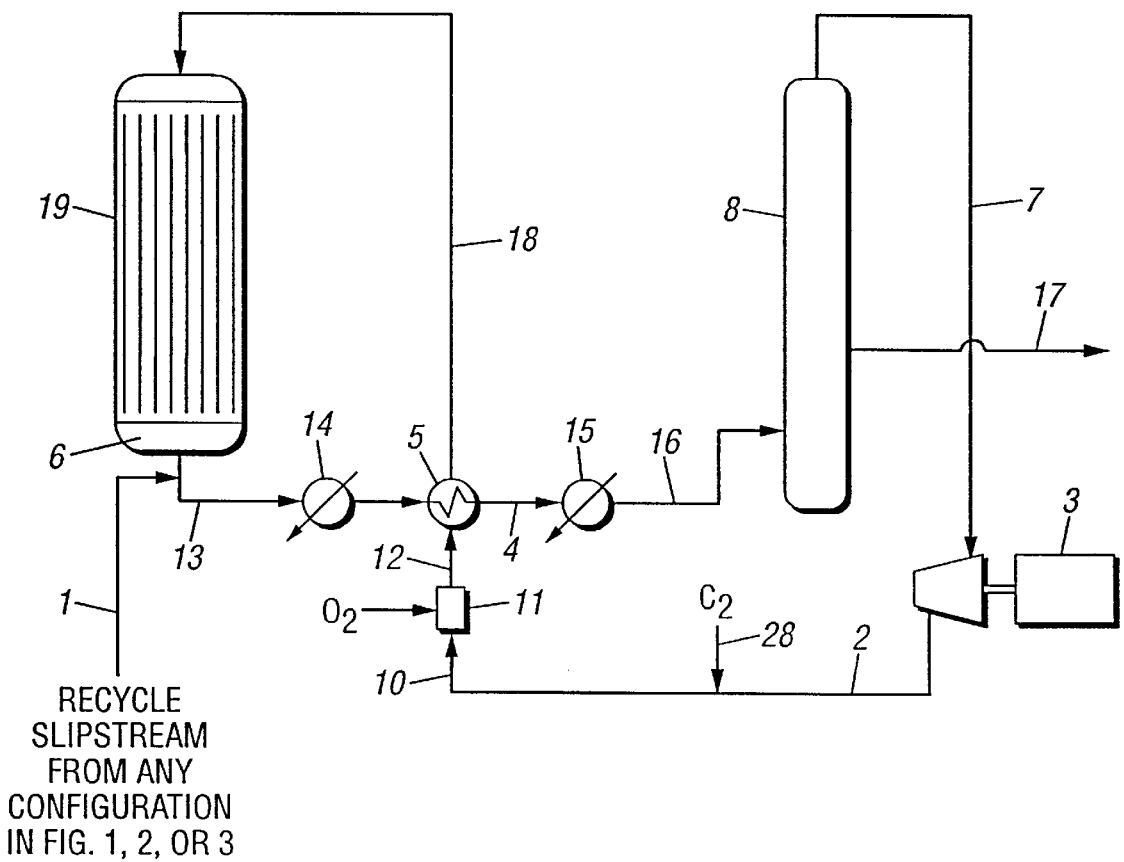
FIG. 4 shows yet another alternative configuration of FIG. 1.

The alternative configuration of FIG. 4 would provide value in situations where modifications to the outlet head must be avoided; the recycle slipstream 1 is introduced into the pipe 13 immediately following the outlet head 6. The disadvantages of this configuration is that aldehyde formation can occur in the head itself, and the oxygen flammable limit at the exit of the reactor tubes would not be reduced unless the outlet head contents are cooled. The advantage of this configuration is a reduced cost of implementation.

In each of the Figures, the recycle slipstream enters the outlet head through a single, simple nozzle. Any number of simple or complex nozzles or other methods of introducing the recycle stream are applicable with the instant invention. The drawings are intended only to relate major hardware components with one another.

The process described above, regardless of the chosen configuration, would not need to be operated throughout a catalyst run. A plant might choose to activate the recycle cooling only when aldehydes begin causing problems in the product streams. Alternatively, a plant might choose to activate the recycle cooling from the beginning of a run in order to maximize the allowable levels of oxygen and ethylene throughout the run. It would also be possible to vary the recycle flow, depending on the degree of cooling desired. Straightforward engineering/thermodynamics equations describe the relationship between plant parameters (outlet head and pipe dimensions and design, product gas flowrate, composition and density, etc.) and the three variables of interest for the disclosed process: reactor outlet gas temperature, recycle gas temperature, recycle ratio, and desired degree of cooling in the outlet head.

Regardless of the recycle ratio employed or the specific configuration chosen (except in the recycle gas compressor case), the amount of gas directed to the absorber section of the plant is not affected by the instant invention, except where the auxiliary recycle cooler is employed, nor is the total amount of heat that is removed by product heat exchangers. Thus, downstream sizing and plant heat balance are not complicated by the instant invention.

Thermodynamic calculations with cost estimates indicate that, for minimal capital outlay and minimal operating costs, the instant invention will accomplish substantial cooling in the outlet head of ethylene oxide reactors. Accordingly, the value of the invention includes the following. Product quality is improved: aldehyde generation and resulting product contamination are minimized, regardless of outlet train design or metallurgy. Catalyst life span is extended until temperatures reach metallurgical or coolant system hardware limits, rather than being dictated by aldehyde restrictions. Full production levels are maintained in situations where aldehyde restrictions would otherwise force a reduction to lower workrates to restrict outlet temperature. The use of high selectivity catalysts is possible in situations where aldehyde concerns might otherwise prevent EO producers from using the high selectivity option. Higher inlet ethylene and/or oxygen levels improve catalyst activity, selectivity and stability. Although the invention can easily be incorporated into grassroots ethylene oxide plants, the invention is especially useful as a retrofit to existing plants where aldehyde problems are known to exist, or where hardware prohibits the use of high selectivity catalysts.

The instant invention is not limited to ethylene oxide manufacture. Elevated outlet temperatures cause problems in any number of exothermic processes (i.e., processes for which heat is produced rather than consumed). Further, product streams from even non-exothermic processes suffer degradation between the catalyst bed and downstream cooling. Therefore, the invention includes not only ethylene oxide, but any process in which the high temperature of the product stream is detrimental.

We claim:

1. A process for the catalytic oxidation of ethylene with molecular oxygen to an ethylene oxide product in a fixed bed reactor wherein a catalyst is disposed in multiple tubes surrounded by a fluid which removes the exothermic heat of reaction, said process comprising providing a cooling zone downstream of said tubes within said reactor, by introducing a cooled recycle slipstream into said zone.

2. The process of claim 1 wherein the temperature of the product exiting said tubes ranges from 232° to 302° C. (450° to 575° F.); wherein the temperature of the cooled recycle slipstream entering said zone ranges from 27° to 232° C. (80° to 450° F.); and wherein the ratio of product exiting said tubes to recycle slipstream ranges from 20:1 to 1:3.

3. The process of claim 1 wherein the cooled recycle slipstream is removed from a primary recycle product stream downstream of a recycle gas compressor and upstream to the addition of oxygen to the recycle product stream.

4. The process of claim 1 wherein the recycle slipstream is removed from at least one location in the product stream between the reactor and an ethylene oxide absorber and cooled prior to being introduced to said cooling zone.

5. A process for the catalytic oxidation of ethylene with molecular oxygen to an ethylene oxide product in a fixed bed reactor wherein a catalyst is disposed in multiple tubes surrounded by a fluid which removes the exothermic heat of reaction, said process comprising introducing a cooled recycle slipstream into a pipe containing the product exiting the reactor.

6. The process of claim 5 wherein the temperature of the product exiting the reactor ranges from 232° to 302° C. (450° to 575° F.); wherein the temperature of the cooled recycle slipstream entering the pipe containing the product ranges from 27° to 232° C. (80° to 450° F.); and wherein the ratio of product to slipstream ranges from 20:1 to 1:3.

7. In a process wherein degradation occurs in a product between a catalytic reaction in a reactor and downstream cooling of the product, due to the high temperature of the product, the improvement comprising recycling a cooled slipstream of the product into the outlet head of the reactor producing the product.

8. The process of claim 7 wherein the process is exothermic.

9. The process of claim 7 wherein the outlet head of the reactor is beneath catalyst containing tubes in the reactor.

10. The process of claim 7 wherein the cooled recycle slipstream is introduced into the reactor with a nozzle system.

* * * * *